Figure 1:
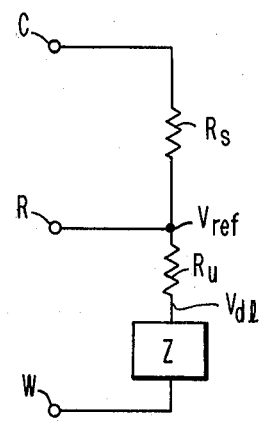

United States Patent [19]

Galwey et al.

[11] 4,348,632
[45] Sep. 7, 1982

[54] SERVOSYSTEM OPERATING ABOUT NOISE COMPONENT ERROR SIGNAL

[75] Inventors: Ronald K. Galwey, Los Gatos; Kay K. Kanazawa, San Jose, both of Calif.

[73] Assignee: International Business Machines Corporation, Armonk, N.Y.

[21] Appl. No.: 187,120

[22] Filed: Sep. 15, 1980

[51] Int. Cl.³ .................. G05F 1/56; C25B 15/00; C25D 21/00
[52] U.S. Cl. ........................ 323/280; 318/632; 318/650; 204/228; 204/231
[58] Field of Search .............. 318/632, 650; 204/195 F, 228, 231; 323/280

[56] References Cited

U.S. PATENT DOCUMENTS

| | | | |
|---|---|---|---|
| 2,545,411 | 3/1951 | Perret-Bit | 318/650 |
| 3,367,859 | 2/1968 | Luden | 318/650 |
| 3,616,286 | 10/1971 | Aylward et al. | 204/24 |
| 3,838,032 | 9/1974 | Yarnilsky | 204/195 |
| 3,855,101 | 12/1974 | Wilson | 204/195 R |
| 3,922,205 | 11/1975 | McLean et al. | 204/1 T |
| 4,028,207 | 6/1977 | Faktor et al. | 204/195 R |

OTHER PUBLICATIONS

"Elimination of iR-Drop in Electrochemical Cells by the Use of a Current-Interruption Potentiostat", D. Britz and W. A. Brocke; Electroanalytical Chemistry & Inter. Electro. #58 (1975 pp. 301-311 ).
"System for the Dynamic Correction of Ohmic Drop in Differential Capacity Measurements", R. Duo, A. Aldaz, J. L. Vazquez and J. Sancho; J. Electroanal. Chem., #73 (1976) pp. 379-382.
"iR Elimination in Electrochemical Cells", D. Britz; J. Electroanal. Chem., #88 (1978) pp. 309-352.
"Dynamic Compensation of the 'Over All' and 'Uncompensated' Cell Resistance in a Two- or Three-Electrode System-Steady State Techniques", C. Yarnitzky and Y. Friedman; Anal. Chem. vol. 47, No. 6, May 1975 pp. 876-880.

Primary Examiner—Gene Z. Rubinson
Assistant Examiner—Eugene S. Indyk
Attorney, Agent, or Firm—George E. Roush

[57] ABSTRACT

The control of the operation of an electric circuit element, such as an electrochemical cell, is performed by positive feedback servocircuitry developing an error signal or inherent noise component, and having algebraic computing capability for developing the compensating control. Current follower circuitry is arranged for developing a potential proportional to the current drawn by the electric circuit element to be controlled. A portion of this potential is algebraically combined with the externally applied operating electric wave. The inherent noise component of the control circuitry is sensed by a high pass filter and an ac-dc converting circuit and thereafter integrated for generating a slowly varying potential for determining the portion of the potential derived by sensing the current. The two potentials are applied to a conventional multiplying circuit and the product potential combined with the operating wave.

10 Claims, 2 Drawing Figures

EQUIVALENT DIAGRAM

SERVOSYSTEM OPERATING ABOUT NOISE COMPONENT ERROR SIGNAL

The invention stems from the endeavors resulting in the copending U.S. patent application Ser. No. 25,415 filed on the 30th day of March, 1979, and a subsequent copending U.S. patent application Ser. No. 49,525 filed on the 18th day of June, 1979.

Field

The invention relates to servocircuitry, and it particularly pertains to such circuitry for compensating for the "ohmic drop" in the operation of electrochemical cells, but it is not limited thereto as it is useful in the control of other electric circuit elements as well.

BACKGROUND

In specific regard to the application of the servocircuitry according to the invention to electrochemical cells, there has been development as evidenced by the above mentioned copending U.S. patent applications, of methods and circuitry for controlling the "ohmic drop". Positive feedback circuitry requiring current interruption and/or the addition of "catalytic" electric energy waves and the like, has been used with minimum satisfaction because of complications necessary in the circuitry and the introduction of annoying transients, together with limitations in bandwidths of the systems.

Two basic dynamic compensation techniques have been predominant in the past. They are, basically, two different methods to obtain an error signal from which the amount of positive feedback is controlled. In the first, a small externally generated ac potential intermixed with cell current data is processed to obtain a positive feedback control signal. In the second technique the cell current is periodically interrupted for a short period. The "double layer voltage" or "barrier layer" equivalent potential within the cell during the zero current interruption period is compared to the input potential to obtain the feedback control signal. The ac method requires not only an ac signal source, but also introduces an extraneous signal into the cell current, which in a real system is non-linearly related to the double layer voltage. An extraneous dc voltage is thereby generated. In addition, it requires signal processing which limits the response time severely. The second technique is bandwidth limited as well, and also requires extremely careful attention to switching transient suppression, switching synchronization and sample and hold synchronization in addition to signal processing.

SUMMARY

The objects of the invention indirectly referred to hereinbefore and those that will appear as the specification progresses are attained in positive feedback servocircuitry interposed in circuit with an electric potential or current controlled electric circuit element, which by way of example only in this case, is an electrochemical cell, for sensing an inherent electric noise component from which an error signal is developed and processed in a circuit having algebraic computing capability for developing the compensating control. Current follower circuitry is arranged for developing a potential proportional to the current drawn by the electric current element to be controlled, for example, the electrochemical cell mentioned. This current inherently has a noise component which is overridden due to the normal electric circuit components themselves and to the driven electric circuit element, especially in the case of the electrochemical cell. A portion of this potential is algebraically combined with the externally applied operating electric wave. The noise component of the circuitry conveying the externally applied wave is extracted and applied to an ac-dc converting circuit and integrated for generating a slowly varying potential for determining the portion of the potential earlier derived for determining the error signal. The two potentials are applied to a conventional multiplying circuit and the product potential combined with the operating wave for compensating the control energy for undesirable varying resistance in the electric circuit element.

PRIOR ART

In addition to the copending U.S. patent application hereinbefore referenced, some prior art will be found in the following U.S. patents:

| | | | |
|---|---|---|---|
| 3,616,286 | 10/1971 | Aylward et al | 204/24 |
| 3,838,032 | 9/1974 | Yarnilsky | 204/195R |
| 3,855,101 | 12/1974 | Wilson | 204/195R |
| 3,922,205 | 11/1975 | McLean et al | 204/1T |
| 4,028,207 | 6/1977 | Faktor et al | 204/195R |

And in the literature:

D. Britz and W. A. Brocke, "Elimination of iR-Drop in Electrochemical Cells By the Use of a Current-Interruption Potentiostat"; Journal of Electroanalytical Chemistry; Vol. 58, 1975, pp 301-311.

C. Yarnitzky and Y. Friedman, "Dynamic Compensation of the 'Overall' and 'Uncompensated' Cell Resistance in a Two- or Three-Electrode System-Steady State Techniques"; Analytical Chemistry; Vol. 47, No. 6; May 1975, pp 876-880.

R. Duo, A. Aldez, J. L. Vazquez and J. Sancho, "System for the Dynamic Correction of Ohmic Drop in Differential Capacity Measurements"; Journal of Electroanalytical Chemistry; Vol 73, 1976, pp 379-382.

D. Britz, "iR Elimination in Electrochemical Cells"; Journal of Electroanalytical Chemistry; Vol. 88, 1978 pp 309-352.

The patent to Aylward and Bregoli, the patent to Yarnilsky and the publication to Britz and Brocke are directed to methods and apparatus for controlling electrochemical cells by interrupting the current flow in the circuitry involved. While there is subcircuitry in each of these references in common with that of the circuitry according to the invention, the computing servocircuitry operating on an error signal derived from internal circuit noise according to the invention is absent.

The patent to Wilson and the publications to Yarnitzky and Friedman and to Duo, Aldez, Vazquez and Sancho are directed to dynamic feedback approaches having some subcircuitry in common with that of the circuitry disclosed in the instant application, the computing servocircuitry operating on an error signal derived from internal circuit noise according to the invention is absent.

The patent to Faktor, Ambridge and Bremmer is directed to a system wherein a current sample is taken for subsequent control. Again the derivation of error signal from the internal noise component as in the invention is totally absent from the arrangement disclosed in this reference. This reference is of interest also in that a semiconductor device arrangement is analyzed in the application, which also is one to which the computing servocircuitry according to the invention is adaptable.

The publication of Britz is of interest in that it reviews a host of methods and circuit arrangements in the prior art and provides a more sophisticated understanding of the electrochemical cell applications. The practical circuit arrangement according to the invention, however, is not found in this otherwise complete treatise.

DRAWING

Figure 2:
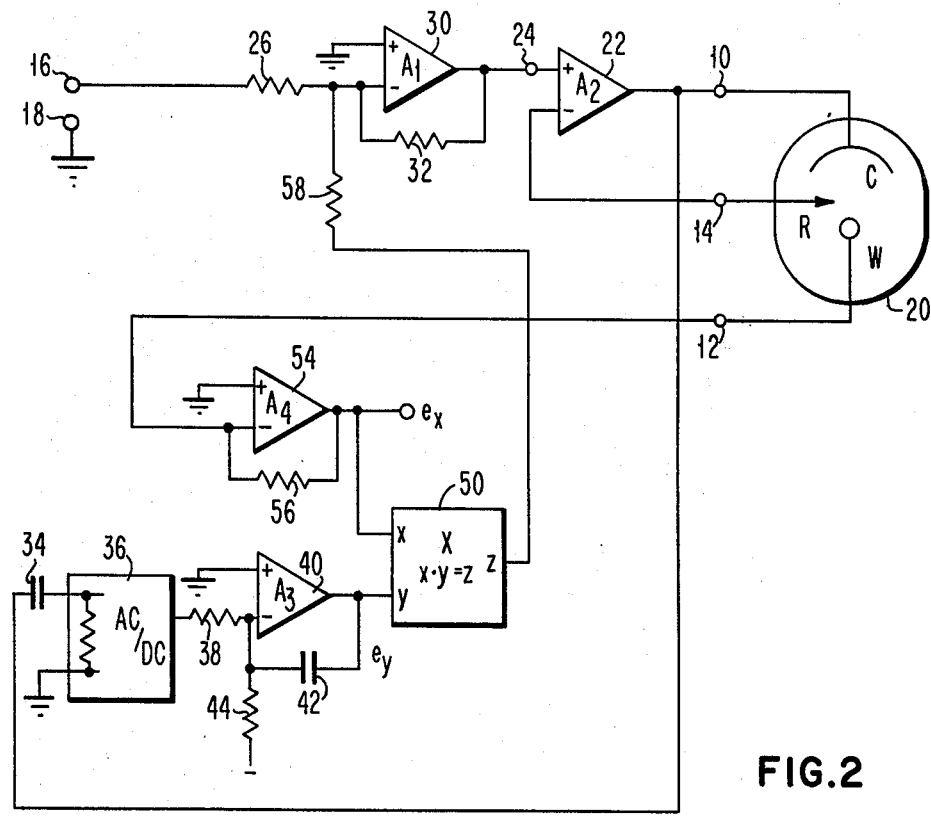

In order that the fullest advantage of the invention obtain in practice, the best mode embodiment thereof, given by way of example only, is described in detail hereinafter with reference to the accompanying drawing forming a part of the specification, and in which:

FIG. 1 is a schematic equivalent diagram of an electrochemical cell useful in an understanding of the application of the invention; and FIG. 2 is a functional diagram of an embodiment of the invention as specifically related to the control of an electrochemical cell.

ENVIRONMENT

While the circuitry according to the invention is useful in many different applications, it has been developed with respect to the control of the electrochemical cell. Therefore, a brief discussion of this particular environment is in order.

The electrical characteristics of the electrochemical interface are explicitly time dependent, resulting primarily from the time dependence of the diffusion of reactant species to the electrode. These electrical characteristics can be analyzed only by knowing the precise time dependence of the potential across that interface. Referring to FIG. 1 for easier understanding, in electrochemical cells there is an unavoidable solution resistance, $R_u$, between the potential-sensing electrode or the reference electrode, RE, and the interface of interest formed between the working electrode, WE, and the solution. As current is drawn through the cell, there is an unavoidable potential drop across this solution resistance, $R_u$, which is an uncompensated resistance.

Although it might seem possible to determine the interface potential $e_D$ from the reference electrode potential $e_R$ by simply substracting from $e_R$ a potential proportional to the current, that is, $e_D = e_R - iR_u$, this requires that the resistance value $R_u$ be accurately known, which is rarely the case. Furthermore, the resistance $R_u$ depends on the field line of the boundary conditions at the electrode R. These boundary conditions are determined from the details of the oxidation/reduction reactions at the electrode R, which are both voltage and time dependent. In summation, the resistance $R_u$ is time-varying and the static compensation discussed here would be of very limited utility. In addition, even if the interface potential and its time dependence could be determined, analytical results coupling the current to potential and time are available only for very well defined potential-time relations.

The interface potential itself must be made to conform to the well defined potential-time variations. One conventional technique for correcting for this uncompensated resistance $R_u$ is to introduce positive feedback into the potentiostat control loop. To achieve compensation, the positive feedback is manually increased until the system is oscillatory, and then feedback is decreased slightly to insure system stability. This method compensates for a fixed amount of cell resistance, and is thus a static correction.

As mentioned previously, the resistance $R_u$ is time dependent, even for a stationary electrode, and for a growing mercury drop electrode would vary strongly with time. To meet the need for dynamic compensation, two basic techniques have been used in the past. They are, basically, two different methods to obtain an error signal from which the amount of positive feedback is controlled. In the first, a small external ac signal is introduced and the resulting ac cell current data is processed to obtain a positive feedback control signal. In the second, the cell current is periodically interrupted for a short period. The double layer voltage, $V_{d1}$, during the zero current interruption period is compared to the input voltage to obtain the feedback control signal. The ac method requires not only an ac signal source, but also has introduced an extraneous signal into the cell current, which in a real system is non-linearly related to the double layer voltage. An extraneous dc voltage is thereby generated. In addition, it requires signal processing which limits the response time severely. The second technique is bandwidth limited as well, and also requires extremely careful attention to switching transient suppression, switching synchronization and sample and hold synchronization in addition to signal processing.

These drawbacks are obviated with the servocircuit according to the invention, wherein the direct current energy is maintained in as steady a state as is possible. Inherent electric noise energy, extremely time dependent as is well known, exists both in the electronic circuitry and in the electric circuit element to be controlled. In the circuitry incorporating the invention, it is not at all necessary to enhance the noise component but even the usual steps may be taken to minimize the effect of internal circuit noise. That the noise is present is recognized and the variation of the noise component in time and in response to circuit operation is utilized in the control of the driven electric circuit element.

DESCRIPTION

A servocircuit arrangement according to the invention is shown in FIG. 2. An electric circuit element connected to output terminals 10 and 12, together with an optional connection to a terminal 14, is operated in response to input electric energy applied at input terminals 16 and 18. As shown herein, the electric circuit element is an electrochemical cell 20 having a counter electrode connected to the terminal 10 and a load electrode connected to the terminal 12 with a reference electrode connected to the terminal 14. For an electrochemical cell, the control potential applied at input terminals 16, 18 is of the order of 0 to ±5 volts ac or dc. The ac potentials, as is well known in the industry, are pulse waves, ramp waves, and sinusoidal waves of electric energy. Similar input waves are used with other electric circuit elements which are readily controlled by circuitry according to the invention. Essentially an electric current flows in an electrochemical cell between the counter and working electrodes and the servocircuit in operation responds to this current flow as determined externally of the cell. It is therefore evident that other electric circuit elements having such a flow of current may be operated with the servocircuit according to the invention, as will be discussed later. The electrochemical cell 20 is conventionally operated with a control amplifier circuit 22 having an output terminal connected to the counter electrode at terminal 10, having a feedback terminal connected to the reference electrode at terminal 14 and having an input terminal 24. Information on this control amplifier circuit and the electrochemical cell is available on reference to the copending U.S. patent application Ser. No. 49,525 mentioned above. The input terminal 24 of the control amplifier is coupled to the input terminal 16 by way of a summing resistor 26, a summing circuit 28 and an operational amplifier circuit arrangement 30-32, the latter components comprising an inverting summing circuit. The ac output of the control amplifier circuit 22, or optionally the output of the summing circuit, is applied by way of a high pass filter comprising a series capacitor 34 and a shunt resistor, the latter usually is one input circuit of a subsequent ac/dc converter circuit 36. The dc output potential of the latter is applied by way of a determining resistor 38 to an integrator circuit 40-42. A resistor 44 and a source of negative potential provides means for biasing the input circuit of the integrator circuit 40-42, the output of which is applied to one input terminal of a multiplying circuit 50. The other input terminal of the circuit 50 is connected to a current follower circuit arrangement 54-56 having one input terminal connected to the load electrode at the terminal 12. The potentials at the input terminals are multiplied and the product of the circuit 50 is applied to the summing circuit by way of an isolating resistor 58.

In operation with a chemical cell 20, the amplifier circuit 22 is the control amplifier for a conventional summing type potentiostat. The circuitry 28-30 32 functions as an inverting summer. The operational amplifier circuit 54-56 is connected as a current follower to produce a voltage $e_x$ proportional to the cell current. A fraction of this voltage $e_x$, is fed back to the summing inverter 30-32 to provide positive feedback. The value of the fraction is determined by the output voltage $e_y$ of the integrator in which the operational amplifier 40-42 is used. The output of the integrator and the output of the current follower are applied to the analog multiplier 50 the output product of which is fed to the inverting summer circuit 30-32.

The ac to dc converter 36 provides a direct potential which is proportional to the magnitude of the high frequencies present in the output of the control amplifier 22. This relatively slowly varying signal is applied to the integrator circuit 40-42. The integrator output $e_y$ controls the gain of the multiplier circuit 50, thus controlling the feedback.

Positive feedback controls using digital feedback techniques are contemplated.

Using this arrangement according to the invention for positive feedback control, extraneous signals, either in the form of added ac or in the form of periodically interrupted current are unnecessary. The circuitry is relatively simple, and servo control, both in the main control loop and in the positive feedback loop, is continuous. This dynamic control does not require determining a set point by allowing the system to go oscillatory, whereby sensitive cells are fully protected. No particular effort additional to normal design need be taken with respect to internal circuit noise, and external wave sources may be used as found.

The servocircuitry according to the invention is not limited to use with an electrochemical cell, but is contemplated for use with other electric circuit elements. For example, a semiconductor device circuit sensitive to changes in temperature as well as current flow is adaptable for connection to terminals 10 and 12 together with a conventional temperature sensing circuit having an output potential applied at the terminal 14. Operation of the circuitry according to the invention is substantially the same.

Furthermore, an amplifier with a single input terminal connected between the terminals 10 and 24 and no connections to the terminal 14 provides a useful circuit arrangement according to the invention. Substantially the same circuit arrangement obtains when the terminal 14 is simply connected to ground.

While the invention has been described in terms of an express embodiment and modifications suggested, it clearly should be understood that those skilled in the art will make changes as required for the application at hand without departing from the spirit and scope of the invention as defined in the appended claims concluding the specification.

The invention claimed is:

1. A closed loop servocircuit arrangement for controlling the operation of an electric circuit element having at least two terminals, comprising
   circuitry for controlling and applying operating energy across said electric circuit element for passing electric current therethrough, which electric current includes an inherent electric noise current component which also manifests an electric noise potential,
   servocircuitry having input terminals coupled to points on said circuitry at which said noise current component and said noise potential components are manifested and having an output terminal at which a processed error signal is presented and combined with said operating energy for controlling the flow of electric current through said electric circuit element,
   said servocircuitry comprising
   an inverting summing circuit having balanced input terminals and having an output terminal,
   a control amplifying circuit having an input terminal connected to said output terminal of said summing circuit, and having an output terminal connected to one terminal of said electric circuit element,
   a current following circuit having an input terminal connected to the other terminal of said electric circuit element and having an output terminal,
   a converting circuit having an input circuit connected to said output terminal of said control amplifying circuit and having an output terminal,
   an integrating circuit having an input terminal connected to said converting circuit and having an output terminal, and
   a multiplying circuit having input terminals individually connected to said output terminals of said current following circuit and said integrating circuit and having a product output terminal connected to one of said input terminals of said summing circuit.

2. A closed loop servocircuit arrangement for controlling the operation of an electrochemical cell having a working electrode, a counter electrode and a reference electrode, comprising
   circuitry for controlling and applying operating energy across said electrochemical cell for passing electric current therethrough, which electric current includes an inherent electric noise current component which also manifests an electric noise potential, servocircuitry having input terminals coupled to points on said circuitry at which said noise current component and said noise potential components are manifested and having an output terminal at which a processed error signal is presented and combined with said operating energy for controlling the flow of electric current through said electrochemical cell, said servocircuitry comprising an inverting summing circuit having balanced input terminals and having an output terminal, a control amplifying circuit having one input terminal connected to said output terminal of said summing circuit, having another input terminal connected to said reference electrode, and having an output terminal connected to said counter electrode of said electrochemical cell, a current following circuit having an input terminal connected to said working electrode of said electrochemical cell and having an output terminal, a converting circuit having an input circuit connected to said output terminal of said control amplifying circuit and having an output terminal, an integrating circuit having an input terminal connected to said converting circuit and having an output terminal, and a multiplying circuit having input terminals individually connected to said output terminals of said current following circuit and said integrating circuit and having a product output terminal connected to one of said input terminals of said summing circuit.

3. A closed loop servocircuit arrangement for controlling the operation of an electric circuit element having at least two terminals, comprising a summing circuit having balanced input terminals and having an output terminal connected to one terminal of said electric circuit element, a current following circuit having an input terminal connected to the other terminal of said electric circuit element and having an output terminal, a converting circuit having an input terminal connected to said output terminal of said summing circuit and having an output terminal, an integrating circuit having an input terminal connected to said converting circuit and having an output terminal, a multiplying circuit having input terminals individually connected to said output terminals of said following circuit and said integrating circuit and having a product output terminal connected to one of said input terminals of said summing circuit for correcting for varying resistance between said terminals of said circuit in operation, and input terminals connected across said balanced input terminals of said summing circuit for operating said electric circuit element.

4. A closed loop servocircuit arrangement as defined in claim 3, and incorporating a circuit component interposed in circuit between said output terminal of said summing circuit and said input terminal of said converting circuit for blocking direct current flow.

5. A closed loop servocircuit arrangement as defined in claim 4, and wherein said circuit component is a capacitor.

6. a closed loop servocircuit arrangement as defined in claim 4, and wherein said circuit component is a highpass filter.

7. A closed loop servocircuit arrangement as defined in claim 6, and wherein said filter circuit comprises a series capacitor coacting with a high impedance input circuit of said converting circuit.

8. A closed loop servocircuit arrangement as defined in claim 3, and wherein said summing circuit comprises potential adding circuit component and an operational amplifying circuit.

9. A closed loop servocircuit arrangement for controlling the operation of an electric circuit element having at least two terminals, comprising an inverting summing circuit having balanced input terminals and having an output terminal, a control amplifying circuit having an input terminal connected to said output terminal of said summing circuit, and having an output terminal connected to one terminal of said electric circuit element, a current following circuit having an input terminal connected to the other terminal of said electric circuit element and having an output terminal, a converting circuit having an input circuit connected to said output terminal of said control amplifying circuit and having an output terminal, an integrating circuit having an input terminal connected to said converting circuit and having an output terminal, a multiplying circuit having input terminals individually connected to said output terminals of said following circuit and said integrating circuit and having a product output terminal connected to one of said input terminals of said summing circuit for correcting for varying resistance between said terminals of said circuit in operation, and input terminals connected across said balanced input terminals of said summing circuit for operating said electric circuit element.

10. A closed loop servocircuit arrangement for controlling the operation of an electrochemical cell having a working electrode, a counter electrode and a reference electrode, comprising an inverting summing circuit having balanced input terminals and having an output terminal, a control amplifying circuit having one input terminal connected to said output terminal of said summing circuit, having another input terminal connected to said reference electrode of said cell and having an output terminal connected to said counter electrode of said cell, a current following circuit having an input terminal connected to said working electrode of said cell and having an output terminal, a converting circuit having an input circuit connected to said output terminal of said control amplifying circuit and having an output terminal, an integrating circuit having an input terminal connected to said converting circuit and having an output terminal, a multiplying circuit having input terminals individually connected to said output terminals of said following circuit and said integrating circuit and having a product output terminal connected to one of said input terminals of said summing circuit for correcting for varying cell resistance in operation, and input terminals connected across said balanced input terminals of said summing circuit for operating said electrochemical cell.

* * * * *